US012544538B2

(12) United States Patent
Vitale et al.

(10) Patent No.: US 12,544,538 B2
(45) Date of Patent: Feb. 10, 2026

(54) INFUSION DEVICE AND METHOD FOR DRUG DELIVERY

(71) Applicants: The Trustees of the University of Pennsylvania, Philadelphia, PA (US); The Children's Hospital of Philadelphia, Philadelphia, PA (US)

(72) Inventors: Flavia Vitale, Wilmington, DE (US); Pedro Gonzalez-Alegre, Wynnewood, PA (US); Timothy H. Lucas, Wynnewood, PA (US)

(73) Assignees: THE TRUSTEES OF THE UNIVERSITY OF PENNSYLVANIA, Philadelphia, PA (US); THE CHILDREN'S HOSPITAL OF PHILADELPHIA, Philadelphia, PA (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 924 days.

(21) Appl. No.: 17/615,131

(22) PCT Filed: May 29, 2020

(86) PCT No.: PCT/US2020/035187

§ 371 (c)(1),
(2) Date: Nov. 30, 2021

(87) PCT Pub. No.: WO2020/243472

PCT Pub. Date: Dec. 3, 2020

(65) Prior Publication Data

US 2022/0226608 A1 Jul. 21, 2022

Related U.S. Application Data

(60) Provisional application No. 62/855,337, filed on May 31, 2019.

(51) Int. Cl.
*A61M 25/00* (2006.01)
*A61M 25/01* (2006.01)

(52) U.S. Cl.
CPC .... *A61M 25/0084* (2013.01); *A61M 25/0026* (2013.01); *A61M 25/0136* (2013.01);
(Continued)

(58) Field of Classification Search
CPC .......... A61M 25/0084; A61M 25/0026; A61M 25/0136; A61M 25/0097; A61M 25/01;
(Continued)

(56) References Cited

U.S. PATENT DOCUMENTS

| | | | | |
|---|---|---|---|---|
| 2002/0026150 A1* | 2/2002 | Palasis | A61M 25/0084 604/164.11 |
| 2002/0120238 A1* | 8/2002 | McGuckin, Jr. | A61B 18/00 606/1 |

(Continued)

OTHER PUBLICATIONS

Extended European Search Report and Preliminary Opinion issued for corresponding EP Application No. 20815628.1 on Jun. 19, 2023.

(Continued)

*Primary Examiner* — Bhisma Mehta
*Assistant Examiner* — Haden Matthew Ritchie
(74) *Attorney, Agent, or Firm* — Howson & Howson LLP

(57) ABSTRACT

A medical device (10) and method for infusing a drug or like substance in vivo within tissue of an organ of a patient are provided. The device (10) includes an outer cannula (12) having a distal and proximal ends (14, 16) and a plurality of microcannulas (20, 22, 24) extending within a length of the outer cannula (12). Each of the microcannulas (20, 22, 24) having a distal end (28) and a proximal end (26) and being movable relative to the outer cannula (12) in a lengthwise direction between retracted and extended positions such that, in the retracted position, the distal ends (28) of the microcannulas (20, 22, 24) are located within the outer (Continued)

cannula (12) and, in the extended position, the distal ends (28) of the microcannulas (20, 22, 24) extend beyond the distal end (14) of the outer cannula (12) in a splayed configuration.

14 Claims, 7 Drawing Sheets

(52) U.S. Cl.
CPC ............... *A61M 2025/0004* (2013.01); *A61M 2025/0042* (2013.01); *A61M 2025/0087* (2013.01); *A61M 2025/0166* (2013.01); *A61M 2210/0693* (2013.01)

(58) Field of Classification Search
CPC .. A61M 2025/0087; A61M 2025/0004; A61M 2025/0086; A61M 2025/0085; A61M 25/0074; A61M 2025/0079; A61M 2025/09116; A61M 25/0071; A61M 5/3295; A61M 5/3298; A61B 2017/00867
See application file for complete search history.

(56) References Cited

U.S. PATENT DOCUMENTS

| | | | | |
|---|---|---|---|---|
| 2004/0064098 | A1 | 4/2004 | Cushieri et al. | |
| 2009/0018638 | A1* | 1/2009 | Shirley ............. | A61M 25/0084 604/164.11 |
| 2010/0168500 | A1 | 7/2010 | Rioux et al. | |
| 2012/0071832 | A1 | 3/2012 | Bunch | |
| 2012/0157917 | A1 | 6/2012 | Schroeder | |
| 2013/0261388 | A1* | 10/2013 | Jenkins .................. | A61B 17/24 600/104 |
| 2013/0281930 | A1 | 10/2013 | Rodenberg et al. | |
| 2016/0287811 | A1* | 10/2016 | Gabin ............... | A61M 25/0084 |
| 2016/0296694 | A1* | 10/2016 | Bankiewicz .......... | A61M 5/142 |
| 2017/0232229 | A1 | 8/2017 | Flores et al. | |
| 2019/0070389 | A1 | 3/2019 | Jayaraman | |

OTHER PUBLICATIONS

International Search Report and Written Opinion of the International Searching Authority issued for International PCT Application No. PCT/US2020/035187 on Sep. 2, 2020.

* cited by examiner

INFUSION DEVICE AND METHOD FOR DRUG DELIVERY

BACKGROUND

Medical procedures may require the delivery or infusion of a drug or like substance directly within the tissue of an organ of a patient in vivo via use of a cannula or like implantable device.

By way of example, the delivery of Adeno Associated Virus (AAV) has been suggested for use in therapeutic intraparenchymal gene transfer to a patient's brain, for instance, for the treatment of Parkinson's disease (PD) and Huntington's disease (HD), and other motor control and like disorders. In these particular examples, the targeted area of the brain is the putamen, a bilateral deep forebrain basal ganglia nuclei involved with motor control.

Efficient transduction of the entire putamen with AAV through a single procedure is challenging. For instance, the location and shape of the putamen may require at least two or three injection sites per putamen thus requiring four or six trajectories of the infusion cannula in total. This necessarily extends the duration and cost of the surgical procedure, and typically will provide suboptimal infusion of the drug within the putamen. In addition, initial trials used relatively low doses which proved inefficient. More recent studies in non-human primates and in human patients with Parkinson's disease (Ann Neurol. 2019 May, 85(5):704-714) indicate that putaminal coverage was less than 50% and that doses of AAV required to achieve full putamenal transduction are significantly higher than originally thought.

SUMMARY OF THE INVENTION

In one aspect, a medical device for infusing a drug, cells, nanoparticles, liposomes, or like substance in vivo within tissue of an organ of a patient is provided. The device includes an outer cannula having distal and proximal ends and a plurality of microcannulas extending within a length of the outer cannula. Each of the microcannulas having a distal end and a proximal end and is movable relative to the outer cannula in a lengthwise direction between retracted and extended positions such that, in the retracted position, the distal ends of the microcannulas are located within the outer cannula and, in the extended position, the distal ends of the microcannulas extend beyond the distal end of the outer cannula in a splayed condition.

According to another aspect, a method of infusing a drug, cells, nanoparticles, liposomes, or like substance in vivo within tissue of an organ of a patient is provided. A medical device is inserted in the patient and is positioned near, adjacent, or within the target organ. The medical device includes an outer cannula having a distal end and a proximal end and a plurality of microcannulas extending within a length of the outer cannula. The distal ends of the microcannulas are retracted within the outer cannula during insertion and positioning of the outer cannula within the patient. Thereafter, the plurality of microcannulas are moved lengthwise relative to the outer cannula to an extended position such that the distal ends of the microcannulas extend beyond the distal end of the outer cannula in a splayed condition. The outer cannula remains in a fixed position relative to the targeted organ as the microcannulas are moved. Thereafter, a pressure-driven drug or like substance is advanced through the microcannulas and infused into the targeted organ simultaneously from each of the plurality of microcannulas.

Other aspects of the invention will be readily apparent from the following detailed description.

DETAILED DESCRIPTION OF THE INVENTION

Definitions

Figure 1:
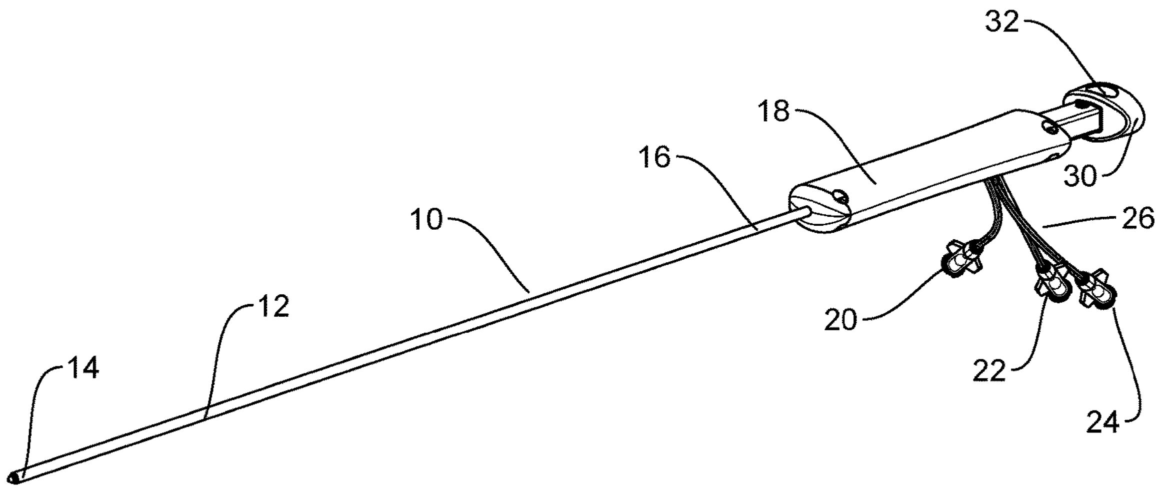
FIG. 1 is a perspective view of an infusion device according to an embodiment.
Figure 2:
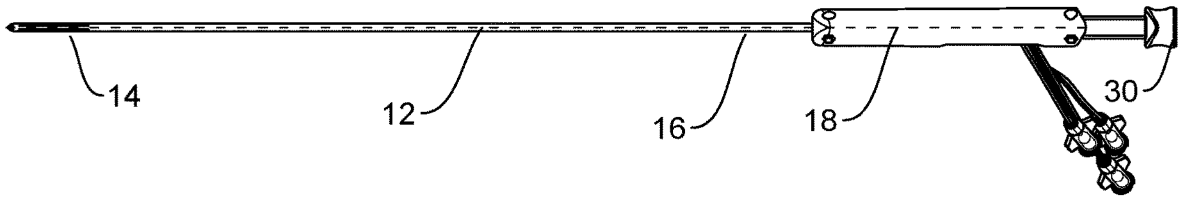
FIG. 2 is a side elevational view of the infusion device of FIG. 1.
Figure 3:
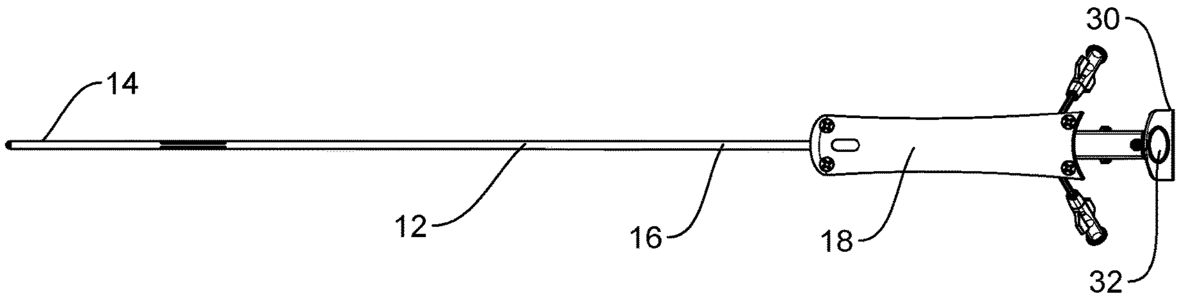
FIG. 3 is a plan view of the infusion device of FIG. 1.

The following definitions are provided. It is to be noted that the term "a" or "an" refers to one or more. As such, the terms "a" (or "an"), "one or more," and "at least one" are used interchangeably herein. It will further be understood that other portions of this specification may contain definitions.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

As used herein, a "subject" or "patient" is a mammal, e.g., a human, mouse, rat, guinea pig, dog, cat, horse, cow, pig, or non-human primate, such as a monkey, chimpanzee, baboon or gorilla. In one embodiment, the patient is a human.

As used herein, the terms "cannula" and "microcannula" refer to tubes of a medical device.

Unless defined otherwise in this specification, technical and scientific terms used herein have the same meaning as commonly understood by one of ordinary skill in the art and by reference to published texts, which provide one skilled in the art with a general guide to many of the terms used in the present application.

A method for AAV delivery to the putamen may use a single infusion cannula providing a single injection point of the drug which necessarily will require at least two, three, or more separate sequential infusions of the drug to different areas of each putamen. Thus, this method necessarily requires repeated re-positioning of the infusion cannula within the brain and a relatively long surgical procedure (i.e., two or more, such as three, trajectories of the infusion cannula in each putamen).

By way of example, AAV delivery to the putamen may take place under magnetic resonance (MR) guidance/monitoring using, for instance, the CLEARPOINT° neuro navigation system marketed by MRI Interventions, Incorporated. The infusion cannula used in this system may be the single lumen SMARTFLOW® neuro ventricular cannula marketed by MRI Interventions, Incorporated. By way of further example, the flow rate through the single tip of the infusion cannula may be 5 μl/min, 10 μl/min or 15 μl/min, or values therebetween. In certain embodiments, a predicted effective volume may be about 900 μl through three separate and sequential infusions per putamen (bilateral infusions).

Description of Embodiments of a Multipoint Injection Device

Embodiments of a medical device are disclosed herein for injecting, delivering, or infusing a drug or like therapeutic substance (i.e., cells, nanoparticles, liposomes, etc.) in vivo within the tissue of a targeted organ of a patient. As an example, the targeted organ may be the brain. In some contemplated embodiments, the medical device may by magnetic resonance imaging (MRI) compatible, for instance, for use in MM-guided injection procedures or the like.

The device includes a single outer cannula or tube that provides multiple spaced-apart points of injection at a distal end thereof which are able to achieve, for instance, full putamenal coverage through a single trajectory of the outer cannula (i.e., via a single positioning of the outer cannula relative to the targeted organ). Thus, such a device should reduce the number of insertions and re-positionings of the outer cannula of the device and should thereby minimize surgical time and cost. In addition, the device may provide increased infusion rates at each surgical trajectory.

By way of example, the device may be used for AAV infusion such as used for intraparenchymal gene transfer. However, the device is not limited to such use and may also be utilized and/or customized for other brain regions targeted for gene therapy (such as the cerebellum) and may also be utilized in other intracerebral drug delivery procedures, such as delivery of chemotherapeutic agents for treating glioblastomas or nanoparticles to deliver nucleic acids and/or proteins. Of course, other uses in other organs of a patient are also possible.

According to one embodiment, the medical device is in the form of an outer tube or cannula that houses multiple separate smaller inner tubes or microcannulas. The outer tube may be a relatively rigid tube with limited flexibility and may extend in a substantially linear path along a central longitudinal axis. Alternatively, the outer tube may extend in a non-linear manner and/or may have some degree of flexibility.

The distal end of each of the smaller tubes or microcannulas provides an injection point for the delivery of drugs or like substances, for instance, for intracerebral drug delivery. Thus, the multiple microcannulas within the outer cannula will provide multiple separate and spaced-apart points of injection to expand coverage of the injection/infusion.

Simply for purposes of example, and not by way of limitation, the device may include a single outer cannula defining a central lumen having a diameter of about 2.5 mm and multiple separate moveable microcannulas, each having an outer diameter of about 500 μm and an inner diameter of about 200 μm, which are located within and extend the length of the lumen of the outer cannula along a longitudinal axis of the outer cannula. In one contemplated embodiment, the device includes three microcannulas. Of course, the device may include just two microcannulas or three or more microcannulas.

According to one contemplated embodiment, the outer cannula is made of nitinol, a nonmagnetic alloy of titanium and nickel that, after being deformed, returns to its original shape upon being reheated. At least a part of the microcannulas may also be made of nitinol. In some embodiments, the outer cannula and microcannulas may be made of other or different materials, for instance, the microcannulas may be made of an elastomer, a flexible plastic, silicone or the like or have an end tip that is made of an elastomer or the like. In some contemplated embodiments, the outer cannula may be more rigid (i.e., less flexible) relative to the inner microcannulas.

As stated above, the distal end of each microcannula provides a port or multiple ports for dispensing, delivering, or infusion a drug or like substance. The multiple ports of the multiple microcannulas may be arranged radially relative to the central longitudinal axis of the outer cannula at the distal end of the outer cannula such that the ports are spaced-apart from each other. The microcannulas may be moved lengthwise relative to the outer cannula so that the microcannulas may be housed entirely within the outer cannula in a retracted position or may be positioned such that each microcannula extends from the distal end of the outer cannula in an extended/deployed position. The distal ends of the microcannulas may possess shape-memory so as to extend from the outer cannula in different predetermined splayed directions so as to increase spacing and infusion coverage. In addition, the distal ends of the microcannulas may be configured to extend in multiple different positions from the outer cannula.

A flow input port at a proximal end of the outer cannula may provide a flow of a drug or like therapeutic substance into the multiple microcannulas such that pressure-driven injection of the substance may occur simultaneously through each of the microcannulas. In addition, a linear actuation system may be provided at the proximal end of the outer cannula to enable the control of movement of the microcannulas relative to the outer cannula. For instance, in an initial position, the multiple microcannulas may be retracted entirely within the outer cannula, and when placed in an injecting or infusing position, the multiple microcannulas may be extended in a spaced-apart or splayed condition from the distal end of the outer cannula to further separate and space-apart the distal ends of the microcannulas.

By way of example, such a medical device may be used as follows. Using standard surgical procedures, the outer cannula may be implanted in a target area relative to an organ, such as the brain, with the microcannulas in a retracted position housed entirely or substantially entirely within the outer cannula. The device may be designed specifically to the targeted anatomical brain area to optimize delivery. Thereafter, the actuation mechanism of the device may be used to advance the microcannulas relatively to the lumen of the outer cannula so that the distal end portions of the microcannulas extend outward in a predetermined splayed condition or pattern from the distal end of the outer cannula to the target areas of the brain or other organ. The flow control system of the device is then activated to provide, for instance, simultaneous, parallel, pressure-driven infusion of a drug dose into and through the microcannulas and into the tissue of the brain or other organ at a plurality of different injection sites in a simultaneous manner. At the end of the infusion, the actuation system may be used to retract the microcannulas inside the lumen of the outer cannula and the outer cannula may then be extracted from the brain or other organ and from the patient.

Thus, compared to single site cannula infusion, embodiments of an injection device disclosed herein eliminate the need for multiple separate sequential injections and repeated re-positioning of an infusion cannula, and thus should significantly reduce the complexity, duration, and cost of a surgical procedure for in vivo infusion of a drug or like therapeutic substance.

Accordingly, the configuration of the infusion sites provided by the multiple microcannulas allows a more uniform distribution of the drug in the tissue in a relatively larger area of the organ in a shorter period of time and thus, maximizes drug delivery and, for instance, AAV transfection efficiency. In addition, as compared to conventional cannulas, the microcannulas should minimize acute trauma and bleeding that can be caused by conventional cannulas. In some contemplated embodiments, the flexible microcannulas may be pre-molded or formed with a memorized and defined radius of curvature thus controlling deflection and splaying of the microcannulas upon being extended from the distal end of the outer cannula thereby further separating and spacing apart the multiple infusion sites in a desired and predetermined pattern corresponding to the shape of the tissue or organ being targeted.

At least some embodiments are for use in drug delivery to a targeted area of the brain, such as the putamen. In addition, other embodiments may be customized for drug delivery to other areas of the brain, such as the deep cerebellar nuclei. Of course, embodiments may be designed and customized for different areas of the brain and for different organs and to deliver and infuse different drugs and substances.

One embodiment of a medical device as described above is shown in FIGS. 1-14. The infusion device 10 has an outer cannula 12 with a distal end 14 and a proximal end 16. A handle 18 or the like is located at the proximal end 16 and includes an activation mechanism. The illustrated infusion device 10 has three separate microcannulas, 20, 22 and 24, extending a length of the outer cannula 12 from the distal end 14 to the proximal end 16. Each of the microcannulas, 20, 22 and 24, has a proximal end 26 into which a supply of drug or like substance may be pressure-driven and injected, and each of the microcannulas, 20, 22 and 24, has a distal end 28 through which the supply of the drug or like substance may be delivered or infused into the tissue of an organ within a patient. As best shown in FIG. 7, each of the microcannulas may have an array of spaced-apart openings along a length thereof for delivery of the fluid, drug or like substance through multiple spaced-apart ports.

Figure 4:
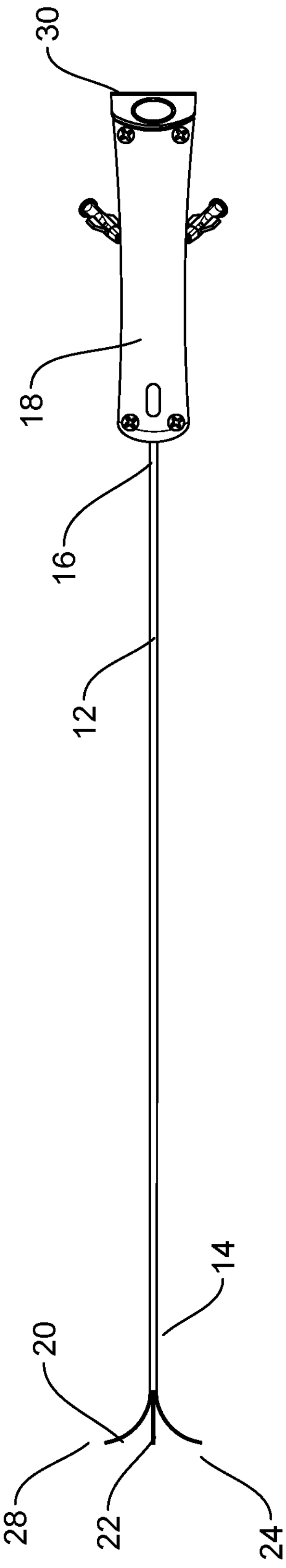
FIG. 4 is a bottom plan view of the infusion device of FIG. 1 with distal ends of a plurality of microcannulas deployed.
Figure 5:
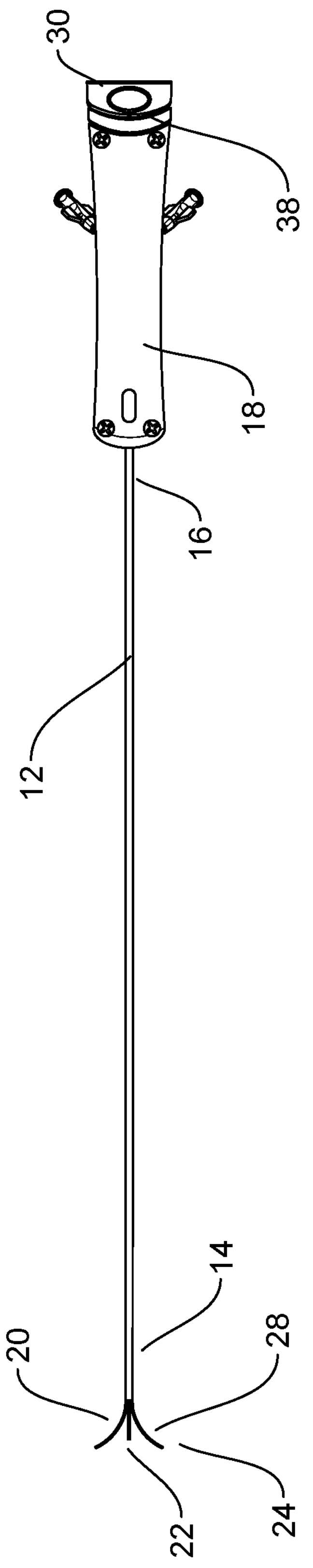
FIG. 5 is a bottom plan view of the infusion device of FIG. 1 with a stopper being utilized and with distal ends of the plurality of microcannulas deployed.
Figure 6:
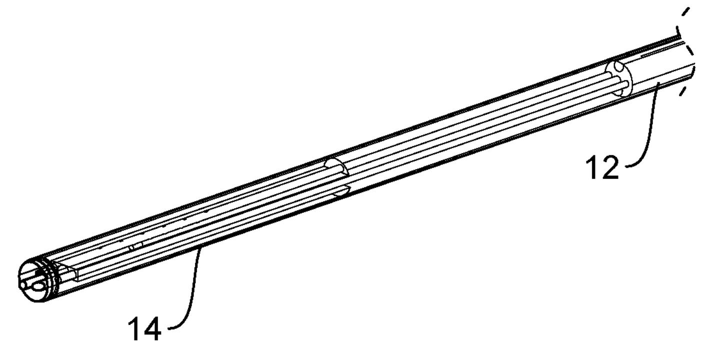
FIG. 6 is a perspective view of a distal end of the infusion device of FIG. 1 with distal ends of a plurality of microcannulas in a retracted position according to an embodiment.
Figure 7:
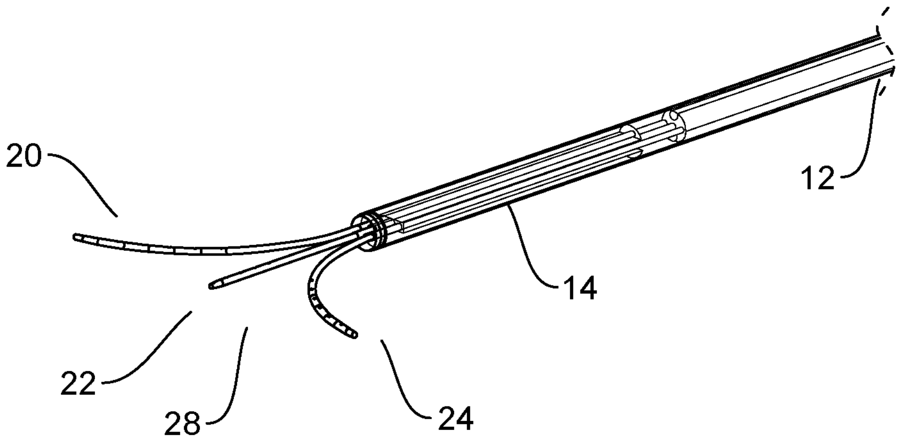
FIG. 7 is a perspective view of a distal end of the infusion device of FIG. 1 with distal ends of a plurality of microcannulas in an extended position according to an embodiment.

In FIGS. 1-3 and 6, the distal ends 28 of the microcannulas, 20, 22 and 24, are in a retracted position within a lumen defined by the outer cannula 12. In contrast, FIGS. 4, 5 and 7 show the distal ends 28 of the microcannulas, 20, 22 and 24, in an extended/deployed position extending beyond the distal end 14 of the outer cannula 12 in a splayed configuration such that injection of a drug or like substance can occur simultaneously via an array of ports extending along three different spaced-apart locations of the tissue, organ, or targeted part thereof. Of course, the number of microcannulas may include only two microcannulas or four or more depending upon intended use.

Figure 8:
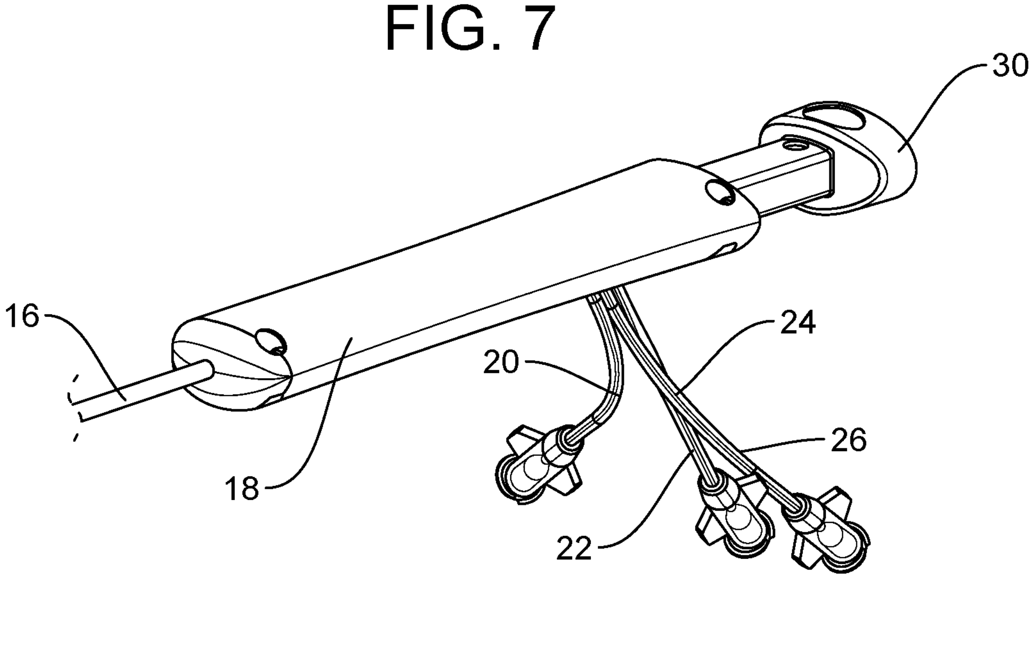
FIG. 8 is a perspective view of the proximal end of the infusion device of FIG. 1 according to an embodiment.
Figure 9:
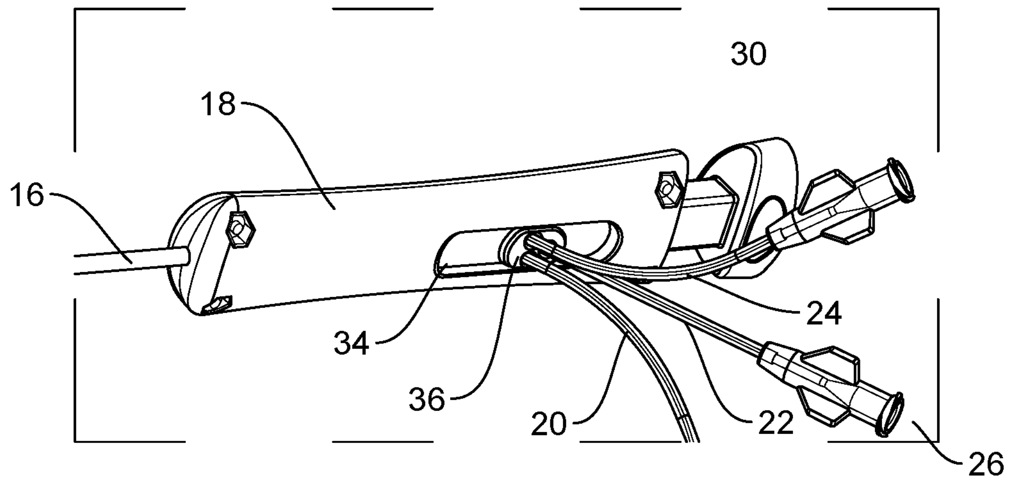
FIG. 9 is a perspective view of the underside of the proximal end of the infusion device of FIG. 1 according to an embodiment.
Figure 10:
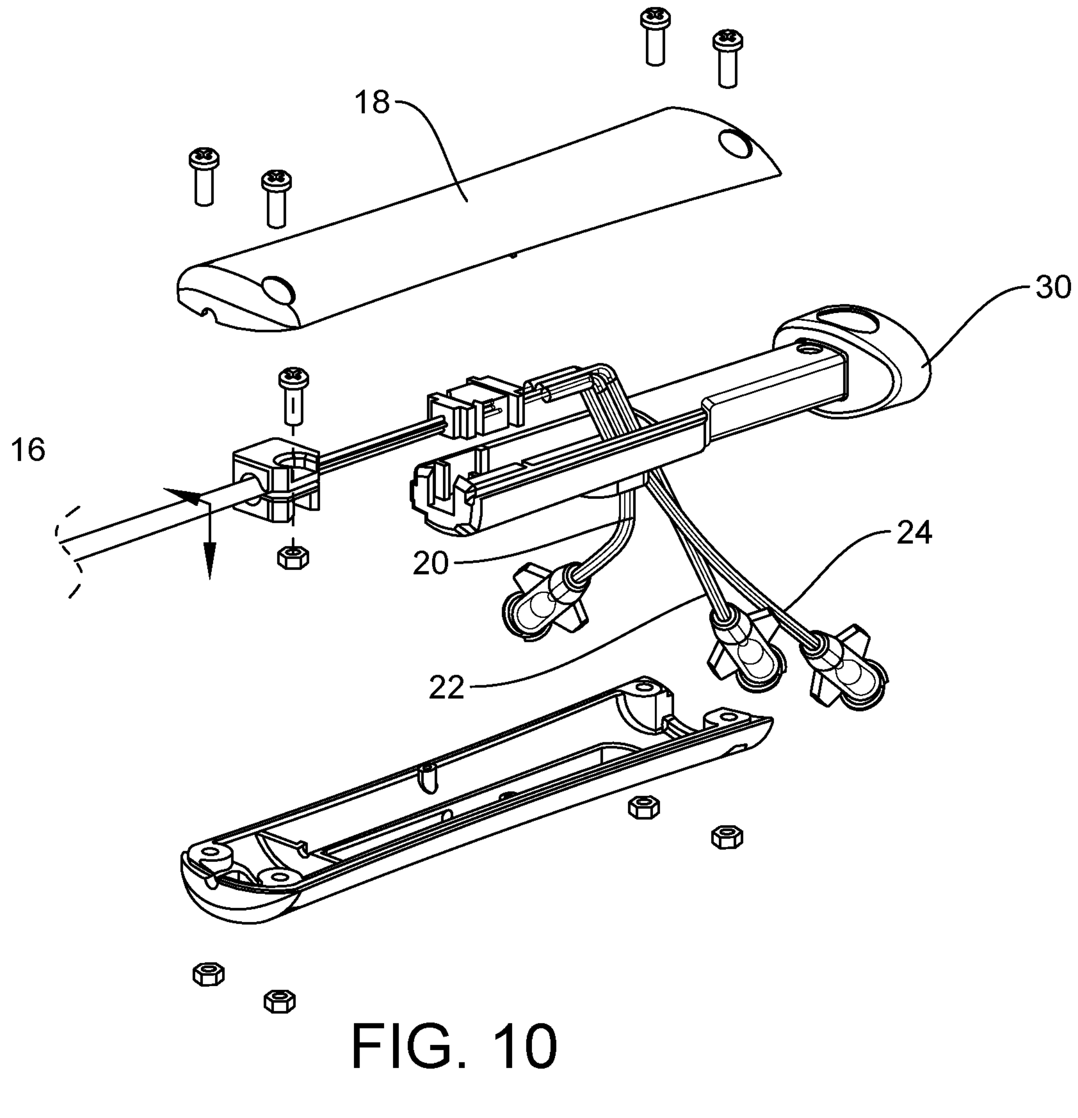
FIG. 10 is an exploded perspective view of the proximal end of the infusion device of FIG. 1 according to an embodiment.

As best shown in FIGS. 8-10, the actuation mechanism is provided by a plunger 30 movable relative to an end of the handle 18. In one contemplated embodiment, the plunger 30 is maintained and locked in a fixed position relative to the handle 18 unless a push button 32 on the plunger 30 is depressed which thereby permits movement of the plunger 30 relative to the handle 18. In other embodiments, a push button 32 may not be utilized. When the plunger 30 is fully extended from the handle 18 (for instance, see FIGS. 1-3 and 6) the microcannulas, 20, 22 and 24, are placed in the retracted position discussed above. However, when the plunger 30 is pushed into the handle 18, the microcannulas, 20, 22 and 24, are moved toward the extended/deployed position discussed above (for instance, see FIGS. 4, 5 and 7).

As best shown in FIG. 9, the extent of the movement of the plunger 30 relative to the handle 18 may be defined by a slot 34 in the base of the handle 18 through which a lateral extension 36 of the plunger 30 housed within the handle 18 extends and is permitted to slide. The lateral extension 36 interconnects the three microcannulas, 20, 22 and 24, to the plunger 30 and defines openings through which the proximal ends of the microcannulas, 20, 22 and 24, extend from the handle 18.

Figure 11:
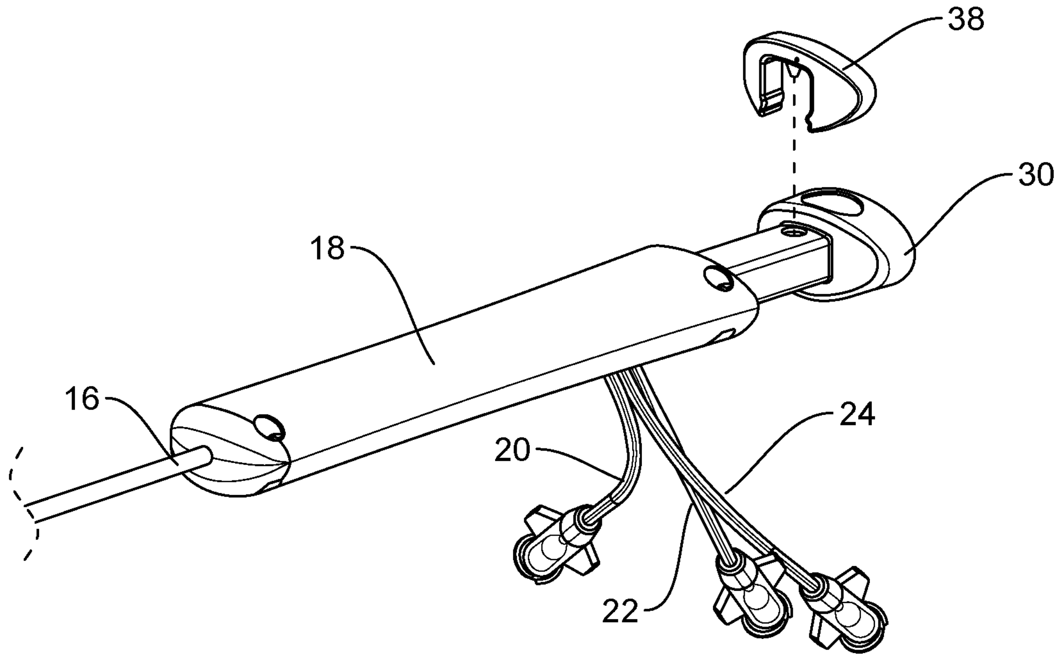
FIG. 11 is a perspective view of the proximal end of the infusion device of FIG. 1 having a stopper according to an embodiment.
Figure 12:
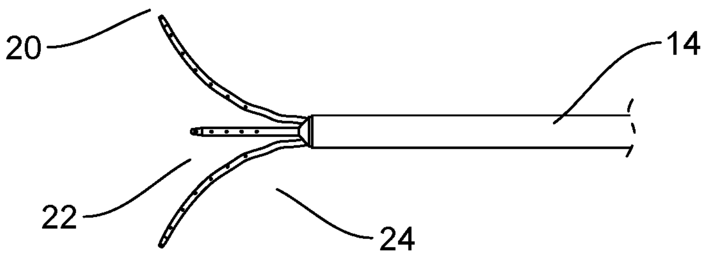
FIG. 12 is a plan view of the distal end of the infusion device of FIG. 11 with microcannulas in an extended position as permitted when the stopper is used.
Figure 13:
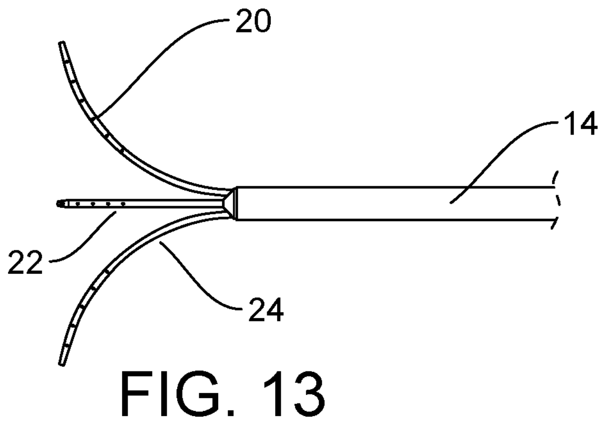
FIG. 13 is a plan view of the distal end of the infusion device of FIG. 11 with microcannulas in an extended position as permitted when the stopper is removed.

In some contemplated embodiments, a mechanism for controlling or limiting the extended positions of the microcannulas may be utilized. For instance, as best shown in FIGS. 5 and 11, a stopper 38 may be located on a throat of the plunger 30 located exterior of the handle 18 to limit the extended position of the microcannulas. For example, while position #1 may correspond to the microcannulas being located entirely within the outer cannula (as shown in FIG. 6), position #2 (as shown in FIG. 12) may correspond to the plunger 30 having a stopper 38 installed thereon and fully pushed into the handle 18 (as limited by the stopper 38), and position #3 (as shown in FIG. 13) may correspond to the plunger 30 with stopper 38 removed and fully pushed into the handle 18. Thus, use of the stopper 38 provides better control of the extent of extension of the microcannulas when in an extended/deployed position. In other embodiments, the position control mechanism may be provided via use of a button, knob, or the like on the handle.

Figure 14:
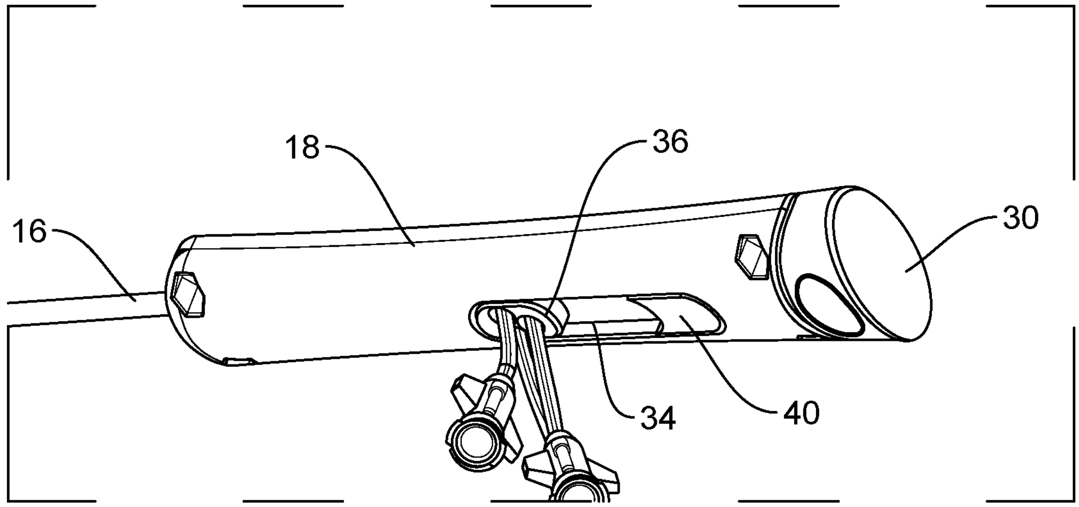
FIG. 14 is a perspective view of the underside of the proximal end of the infusion device of FIG. 1 having a stopper according to an embodiment.

As another alternative as shown in FIG. 14, a stopper 40 may be located in one of the ends of the slot 34 of the handle 18 to limit movement of the lateral extension 36 of the plunger 30 relative to the handle 18 to control the extent of extension of the microcannulas when in an extended position. This is merely provided by way of example and other mechanism may be provided to control the position and extent of extension of the microcannulas.

Although not illustrated, a four-way valve, junction, or "pig-tail" connector may be connected to the proximal ends of the microcannulas, 20, 22 and 24, to equally disperse a supply of incoming drug or like substance from a single input into the three microcannulas, 20, 22 and 24. Thus, the drug or like substance may be simultaneously delivered/injected from all three splayed distal ends of the microcannulas, 20, 22 and 24.

Description of Embodiments of a Method of Using the Multipoint Injection Device

A method of infusing a substance (i.e., drug, cells, nanoparticles, liposomes, etc.) in vivo with the infusion device described above may include the following process steps. The infusion device 10 is inserted/implanted within the brain or other organ of a subject with a guidance system, for example, under MRI guidance using commercial MRI Interventions guidance system. Of course, other guidance systems may be used. In this step, the microcannulas are in the retracted position described above. Thereafter, the three moveable microcannulas are deployed be being positioned in the extended position (such as by pushing the plunger 30 into the handle 18 as described above). After deployment of the microcannulas, a fluid (such as containing a contrast agent), drug or like substance is injected into the brain or other organ from the three microcannulas. The injected volume may be visualized with MRI or the like. All of the above occurs with a single insertion and without repositioning the outer cannula (i.e. a single trajectory of the outer cannula of the device).

Figure 15:
FIG. 15 is an image of the infusion device located within a brain and the fluid having been injected.

FIG. 15 is an image of an experiment showing the injection device 10 located within the brain of a non-human primate and fluid with a contrast agent infused therein.

As discussed above, the injection device 10 may be used for delivering a therapeutic substance alone, or in a treatment regimen optionally in combination with other active substances, to tissue of an organ of a patient in need thereof. Examples of such therapeutic substances which may be delivered include, e.g., oncolytic therapy, gene therapy, antisense therapy, immunotherapy, delivery of small molecule drugs, delivery of anesthesia, pain medication, or chemotherapies. This device may be useful in treating patients with a variety of indications including, without limitation, primary or metastatic cancers, lysosomal storage diseases, movement disorders including but not limited to primary essential tremor, Parkinson's Disease, Alzheimer's Disease, mucopolysaccharidoses (MPS) which include seven sub-types: MPS I, MPS II, MPS III, MPS IV, MPS VI, MPS VII, and MPS IX; spinal muscular atrophy (SMA), Batten disease (neuronal ceroid lipofuscinoses, or NCLs); transmissible spongiform encephalopathies (e.g., Creutzfeldt-Jacob disease), amyotrophic lateral sclerosis (ALS), multiple sclerosis, Huntington disease, Canavan's disease, traumatic brain injury, spinal cord injury, migraine, lysosomal storage diseases, stroke, and infectious diseases affecting the central nervous system.

The device may be used for delivery of an active drug(s) or other therapeutic substance (e.g., gene therapy vector, antibody, peptide, cells, nanoparticles, liposomes, proteins, peptides or other therapeutic biologics, etc.) which is in a pharmaceutically acceptable suspension or solution (e.g., an aqueous based composition), which optionally contains conventional pharmaceutical ingredients, such as preservatives, or chemical stabilizers.

Suitably, the composition may contain water (e.g., saline), a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, for delivery, a pH within this range may be desired. However, other pHs within the broadest ranges and these subranges may be selected for other route of delivery.

A suitable surfactant, or combination of surfactants, may be selected from among non-ionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

In one example, the formulation may contain, e.g., buffered saline solution comprising one or more of sodium chloride, sodium bicarbonate, dextrose, magnesium sulfate (e.g., magnesium sulfate·7H2O), potassium chloride, calcium chloride (e.g., calcium chloride·2H2O), dibasic sodium phosphate, and mixtures thereof, in water. Suitably, for intrathecal delivery, the osmolarity is within a range compatible with cerebrospinal fluid (e.g., about 275 to about 290); see, e.g., emedicine.medscape.com/-article/2093316-overview. Optionally, for delivery using the device, a commercially available diluent may be used as a suspending agent, or in combination with another suspending agent and other optional excipients. See, e.g., Elliotts B® solution [Lukare Medical]. The pH of Elliotts B Solution is 6 to 7.5, and the osmolarity is 288 mOsmol per liter (calculated). In certain embodiments, the composition containing the rAAVhu68.SMN1 gene is delivered at a pH in the range of 6.8 to 8, or 7.2 to 7.8, or 7.5 to 8. For intrathecal delivery, a pH above 7.5 may be desired, e.g., 7.5 to 8, or 7.8.

In certain embodiments, the formulation may contain a buffered saline aqueous solution not comprising sodium bicarbonate. Such a formulation may contain a buffered saline aqueous solution comprising one or more of sodium phosphate, sodium chloride, potassium chloride, calcium chloride, magnesium chloride and mixtures thereof, in water, such as a Harvard's buffer. The aqueous solution may further contain Kolliphor® P188, a poloxamer which is commercially available from BASF which was formerly sold under the trade name Lutrol® F68. The aqueous solution may have a pH of 7.2.

In another embodiment, the formulation may contain a buffered saline aqueous solution comprising 1 mM Sodium Phosphate (Na3PO4), 150 mM sodium chloride (NaCl), 3 mM potassium chloride (KCl), 1.4 mM calcium chloride (CaCl2), 0.8 mM magnesium chloride (MgCl2), and 0.001% Kolliphor® 188. See, e.g., harvardapparatus.com/harvard-apparatus-perfusion-fluid.html. In certain embodiments, Harvard's buffer is preferred due to better pH stability observed with Harvard's buffer.

In certain embodiments, the device provided herein avoids the need for one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA. In another embodiment, a composition may include includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo.

Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

Intravenous (IV) contrast may be administered prior to or during insertion of the device. The patient may be anesthetized, intubated, and positioned on the procedure table.

Suitable volumes for delivery of these doses and concentrations may be determined by one of skill in the art. For example, for AAV intraputaminal delivery in adults, the flow rate through the microcannulas of the above referenced embodiments may be 1 μl/min to 15 μl/min, or values therebetween, e.g., about 5 μl/min, about 10 μl/min or about 15 μl/min, and the predicted effective volume may be about 900 μl. In certain embodiments, flow rates of 1 μl/min to 5 μl/min may be selected. In certain embodiments, flow rates of 1 μl/min to 10 μl/min may be selected. In certain embodiments, flow rates of 5 μl/min to 10 μl/min may be selected. In certain embodiments, flow rates of 5 μl/min to 15 μl/min may be selected. Other suitable volumes and dosages may be determined. These flow rates and volumes may also be utilized for other compositions delivered via the device. These flow rates and volumes may also be used for delivery to other regions of the brain as described herein. The dosage will be adjusted to balance the therapeutic benefit against any side effects and such dosages may vary depending upon the therapeutic application for which the recombinant vector is employed. By way of example and not by way of limitation, volumes of about 1 μL to 150 mL may be selected, with the higher volumes being selected for adults. For example, for newborn infants a suitable volume may be about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. Other suitable volumes and dosages may be determined.

In certain embodiments, a gene therapy vector is an AAV-based vector having a dose of about 1×109 GC/g brain mass to about 1×1012 GC/g brain mass. In certain embodiments, the dose may be in the range of about 3×1010 GC/g brain mass to about 3×1011 GC/g brain mass. In certain embodiments, the dose may be in the range of about 5×1010 GC/g brain mass to about 1.85×1011 GC/g brain mass. In one embodiment, the vector may be delivered in doses of from at least about least 1×109 GCs to about 1×1015, or about 1×1011 to 5×1013 GC. Still other suitable doses of gene therapy vectors or non-vector delivery systems may be readily selected by one of skill in the art.

Similarly, other compositions may be delivered via the device for treatment of various injuries, diseases, conditions or disorders.

While the invention has been described with reference to particular embodiments, it will be appreciated that modifications can be made without departing from the spirit of the invention. Such modifications are intended to fall within the scope of the appended claims.

What is claimed is:

1. A medical device (10) for infusing a drug, cells, nanoparticles or liposomes in vivo to tissue of an organ of a patient, comprising: an outer cannula (12) having a distal end (14) and a proximal end (16); a handle (18) to which the proximal end (16) of the outer cannula (12) is fixed; and a plurality of microcannulas (20, 22, 24) extending within a length of said outer cannula (12), each of said microcannulas (20, 22, 24) having a distal end (28) and a proximal end (26) and defining a lumen extending therethrough; wherein said plurality of microcannulas (20, 22, 24) are movable relative to said outer cannula (12) in a lengthwise direction between retracted and extended positions such that, in said retracted position, said distal ends (28) of said microcannulas (20, 22, 24) are located within said outer cannula (12) and, in said extended position, said distal ends (28) of said microcannulas (20, 22, 24) extend beyond said distal end (14) of said outer cannula (12) in a splayed condition; wherein said handle (18) includes an actuator interconnected to the proximal ends (26) of said plurality of microcannulas (20, 22, 24) and movable relative to said outer cannula (12) for advancing and retracting said plurality of microcannulas (20, 22, 24) lengthwise relative to said outer cannula (12); wherein the actuator comprises a plunger (30) extending from a free end of the handle (18) and being slidable relative to and within said handle (18) and not extending within said outer cannula (12); wherein the handle (18) includes a longitudinally-extending slot (34) and the plunger (30) includes a lateral extension (36) that extends within the slot (34) such that the slot (34) and lateral extension (36) limit the extent of sliding motion of the plunger (30) relative to the handle (18) along a linear path; and wherein the proximal ends (26) of said plurality of microcannulas (20, 22, 24) are interconnected to said lateral extension (36) and extend through said lateral extension (36) such that the proximal ends (26) of said microcannulas (20, 22, 24) and the lumens thereof extend out of and exit said handle (18) through the lateral extension (36) of the plunger (30) and thus through and out of the slot (34) in which the lateral extension (36) extends.

2. The medical device (10) according to claim 1, wherein the proximal ends (26) of said plurality of microcannulas (20, 22, 24) are connected to a pressure-driven supply of the drug, cells, nanoparticles or liposomes.

3. The medical device (10) according to claim 1, further comprising a position control mechanism for adjusting the extent of sliding motion of the plunger (30) relative to the handle (18).

4. The medical device (10) according claim 1, wherein each of the distal ends (28) of said microcannulas (20, 22, 24) includes an array of spaced-apart ports along a length thereof.

5. The medical device (10) according to claim 1, wherein the distal ends (28) of said microcannulas (20, 22, 24) become splayed in a predetermined pattern when in said extended position.

6. The medical device (10) according to claim 1, wherein said microcannulas (20, 22, 24) are flexible and said outer cannula (12) is less flexible than said microcannulas (20, 22, 24).

7. The medical device (10) according to claim 6, wherein said microcannulas (20, 22, 24) are made of an elastomer.

8. The medical device (10) according to claim 6, wherein said outer cannula (12) is made of a metal or metal alloy.

9. The medical device (10) according to claim 6, wherein the distal ends (28) of said microcannulas (20, 22, 24) have shape memory such that, in said extended position, the distal ends (28) splay in a predetermined pattern as extended from the distal end (14) of said outer cannula (12).

10. A method of infusing a drug, cells, nanoparticles or liposomes in vivo within tissue of an organ of a patient, comprising the steps of: inserting a medical device (10) within the patient adjacent the organ, the medical device (10) including an outer cannula (12) having a distal end (14) and a proximal end (16), a handle (18) to which the proximal end (16) of the outer cannula (12) is fixed, and a plurality of microcannulas (20, 22, 24) each defining a lumen extending within a length of said outer cannula (12), distal ends (28) of said microcannulas (20, 22, 24) being retracted within said outer cannula (12) during said inserting step, the handle (18) including an actuator interconnected to the proximal ends (26) of the plurality of microcannulas (20, 22, 24) and movable relative to the outer cannula (12) for advancing and retracting the plurality of microcannulas (20, 22, 24) lengthwise relative to the outer cannula (12), the actuator comprising a plunger (30) extending from a free end of the handle (18) and being slidable relative to and within said handle (18) and not extending within said outer cannula (12), the handle (18) including a longitudinally-extending slot (34) and the plunger (30) including a lateral extension (36) that extends within the slot (34) such that the slot (34) and lateral extension (36) limit the extent of sliding motion of the plunger (30) relative to the handle (18) along a linear path, and the proximal ends (26) of the plurality of microcannulas (20, 22, 24) are interconnected to the lateral extension (36) and extend through the lateral extension (36) such that the proximal ends (26) of the microcannulas (20, 22, 24) and the lumens thereof extend out of and exit the handle (18) through the lateral extension (36) of the plunger (30) and thus through and out of the slot (34) in which the lateral extension (36) extends; moving said plurality of microcannulas (20, 22, 24) lengthwise relative to said outer cannula (12) to an extended position by sliding the plunger relative to the handle such that the distal ends (28) of the microcannulas (20, 22, 24) extend beyond the distal end (14) of the outer cannula (12), the outer cannula (12) remaining in a fixed location relative to the organ during said moving step and the plurality of microcannulas (20, 22, 24) being flexible and splaying from each other and the distal end (14) of the outer cannula (12) during said moving step; and after said moving step, infusing a pressure-driven drug, cells, nanoparticles or liposomes into the organ simultaneously from the plurality of microcannulas (20, 22, 24).

11. The method according to claim 10, further comprising the steps of:

retracting the plurality of microcannulas (20, 22, 24) into the outer cannula (12) after said infusing step; and after said retracting step, withdrawing the outer cannula (12) from the patient.

12. The method according to claim 10, wherein said inserting step is accomplished with the assistance of magnetic resonance guidance.

13. The method according to claim 10, wherein the organ is the brain.

14. The method according to claim 13, wherein the drug, cells, nanoparticles or liposomes is Adeno Associate Virus for therapeutic gene transfer to the putamen of the brain.

* * * * *